(12) United States Patent  
Omar-Pasha et al.

(10) Patent No.: US 9,168,368 B2  
(45) Date of Patent: Oct. 27, 2015

(54) METHOD FOR APPLYING PULSED RADIO FREQUENCY ENERGY TO THE SPINAL CANAL

(75) Inventors: Omar Omar-Pasha, Hamburg (DE); Uwe Stumpp, Frittlingen (DE); Christian Mantsch, Minden (DE)

(73) Assignees: OMT GMBH (DE); Omar Omar-Pasha (DE)

( * ) Notice: Subject to any disclaimer, the term of this patent is extended or adjusted under 35 U.S.C. 154(b) by 0 days.

(21) Appl. No.: 11/049,247

(22) Filed: Feb. 2, 2005

(65) Prior Publication Data

US 2005/0137667 A1 Jun. 23, 2005

Related U.S. Application Data

(63) Continuation-in-part of application No. 10/844,639, filed on May 13, 2004.

(30) Foreign Application Priority Data

May 27, 2003 (DE) .............................. 203 08 422 U  
Aug. 4, 2003 (DE) .............................. 203 12 110 U  
Jan. 20, 2004 (DE) ..................... 20 2004 000 852 U

(51) Int. Cl.
| | |
|---|---|
| *A61N 1/34* | (2006.01) |
| *A61N 1/05* | (2006.01) |
| *A61N 1/06* | (2006.01) |
| *A61B 18/00* | (2006.01) |
| *A61N 1/36* | (2006.01) |
| *A61N 1/40* | (2006.01) |

(52) U.S. Cl.  
CPC ............ *A61N 1/0529* (2013.01); *A61N 1/0551* (2013.01); *A61N 1/06* (2013.01); *A61B 2018/0044* (2013.01); *A61B 2018/00678* (2013.01); *A61B 2018/00714* (2013.01); *A61N 1/36071* (2013.01); *A61N 1/40* (2013.01)

(58) Field of Classification Search  
USPC .......... 607/40, 41, 3, 46, 48, 50, 72, 101, 154  
See application file for complete search history.

(56) References Cited

U.S. PATENT DOCUMENTS

| | | |
|---|---|---|
| 4,044,774 A | 8/1977 | Corbin et al. |
| 4,379,462 A | 4/1983 | Borkan et al. |
| 4,607,639 A * | 8/1986 | Tanagho et al. ................ 607/40 |

(Continued)

FOREIGN PATENT DOCUMENTS

| | | |
|---|---|---|
| DE | 3602219 | 7/1987 |
| EP | 0 644 736 | 10/1998 |

(Continued)

*Primary Examiner* — Kennedy Schaetzle  
(74) *Attorney, Agent, or Firm* — Cohen & Grigsby, P.C.

(57) ABSTRACT

A flexible catheter includes two electrical contacts in a distal region of the catheter and a distal aperture of a hose line. The electrical contacts are connected to a high frequency pulse generator for applying pulsed radio frequency energy for nerve stimulation. A temperature sensor is located in the distal region of the catheter. The flexible catheter is inserted into a region in the spinal canal and the pulsed radio frequency generator is operated, thereby applying pulsed radio frequency energy to a localized region to be treated. The temperature at the distal region of the catheter can also be monitored, and the pulsed radio frequency energy is applied in dependence on the monitored temperature. With the catheter, pain and other medical conditions being related to and influenced by a nervous system are treated.

9 Claims, 5 Drawing Sheets

(56) References Cited

U.S. PATENT DOCUMENTS

| | | | |
|---|---|---|---|
| 4,907,589 A * | 3/1990 | Cosman | 606/34 |
| 5,081,990 A | 1/1992 | Deletis | |
| 5,374,285 A | 12/1994 | Vaiani et al. | |
| 5,423,877 A | 6/1995 | Mackey | |
| 5,713,923 A | 2/1998 | Ward et al. | |
| 6,146,380 A | 11/2000 | Racz et al. | |
| 6,208,881 B1 | 3/2001 | Champeau | |
| 6,246,912 B1 * | 6/2001 | Sluijter et al. | 607/100 |
| 6,322,549 B1 * | 11/2001 | Eggers et al. | 604/500 |
| 7,167,756 B1 | 1/2007 | Torgerson et al. | |
| 2001/0023348 A1 | 9/2001 | Ashley et al. | |

FOREIGN PATENT DOCUMENTS

| | | |
|---|---|---|
| EP | 1 145 731 | 10/2001 |
| EP | 1 181 947 | 2/2002 |
| WO | WO 92/07605 | 5/1992 |
| WO | 01/83029 A1 | 11/2001 |

\* cited by examiner

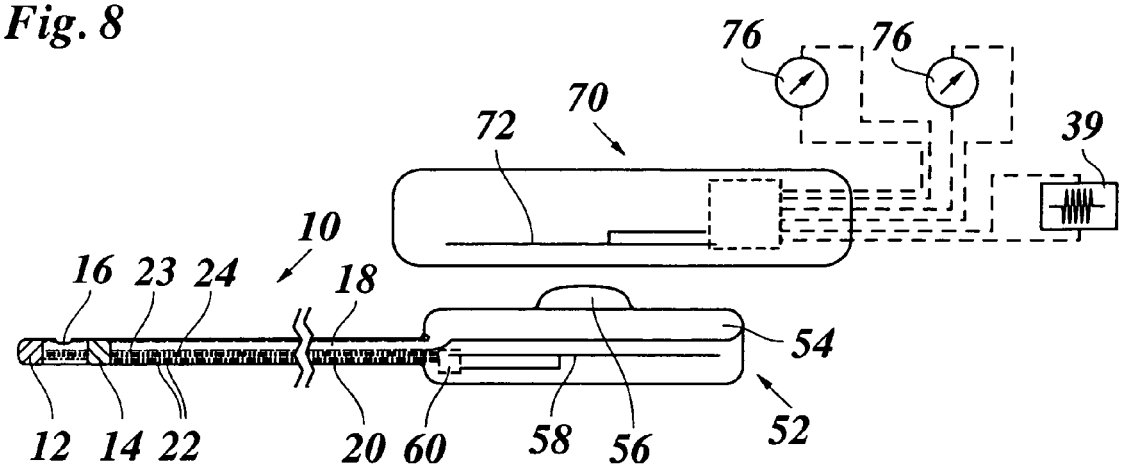
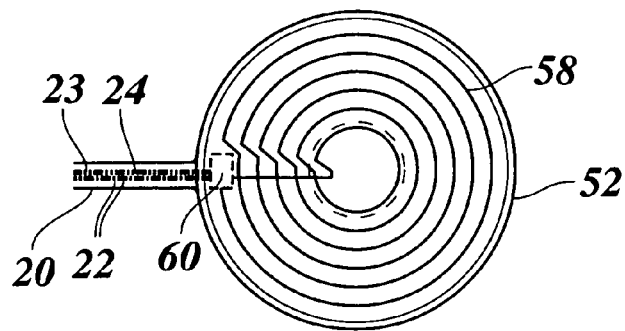
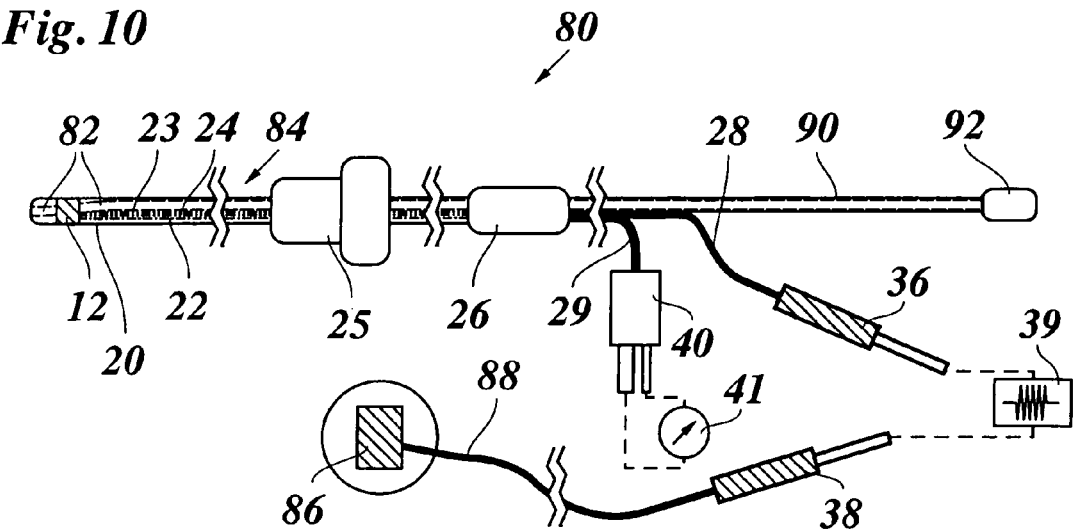

METHOD FOR APPLYING PULSED RADIO FREQUENCY ENERGY TO THE SPINAL CANAL

REFERENCE TO RELATED APPLICATION

The present application is a continuation-in-part of U.S. patent application Ser. No. 10/844,639, filed May 13, 2004.

BACKGROUND OF THE INVENTION

1. Field of the Invention

This invention relates to nerve stimulation by electrically applying high frequency (radio frequency) energy to a localized region of a body. In particular, this invention relates to a flexible catheter or lead for treatment of a nervous system. More particularly this invention relates to a flexible epidural catheter and a method for applying pulsed radio frequency electrical energy to a region in the spinal canal. A fully implantable embodiment of the catheter further comprises a transducer being adapted to be subcutaneously implanted.

2. Description of Related Art

Catheters are known technical medical products which are manufactured for various intended purposes of usage in diagnostics or therapy. For instance, epidural catheters are known which can be inserted by a physician into the epidural space in the region of the spinal canal so as to be able to inject pain-killing drugs, for example. Such a method is particularly applied in treatment of chronic pain. The catheter can remain in the body for a time period of 1 to 30 days, for example, and the injection of the drugs can be effected through external or implanted pumps.

Instead of catheters also electrodes are used in therapy of chronic pain. Thus, electrodes for implantation are known, which are connected to a pulse generator for permanent stimulation of the spinal cord or the nerves. There are also known electrodes for stimulation which are connected to a transducer that is to be subcutaneously implanted. In this case the pulses of the generator are transmitted inductively to the transducer through the skin of the patient.

Moreover, special needles are known which are connected to a generator of pulsed high frequency. Such special needles and high frequency generators are used to trigger the release of pain-inhibiting substances in the spinal cord by selectively stimulating nerves, thereby effecting a pain treatment.

However, usage of these rigid special needles is frequently limited due to anatomical reasons or is avoided because of the risk of injury at introducing the special needles.

From European patent application EP 1 181 947 A2 an epidural catheter is known having at least three electrodes arranged in line. The electrodes serve to electrically stimulate nerves or the spinal cord. A channel for administration of drugs can be provided to allow for injecting pain-killing drugs in addition to the electrical stimulation of the spinal cord.

With the previously mentioned apparatuses operating with electrical stimulation by means of pulses or, in the case of the special needles, by means of pulsed high frequency, control of the effect of the stimulation is solely by feedback from the patient. The mode and intensity of the stimulation is determined on an empirical basis. However, an upper limit of the intensity of the stimulation is given by possible damage or destruction of the tissue and varies depending on the location and the design of the catheter or special needles and on the structure of the surrounding tissue. Hence, there is no definite correlation between the parameters of the applied pulses and the limit where damage occurs, so that a margin of safety has to be observed. The mentioned deficiencies also pertain to the documents acknowledged below.

U.S. Pat. No. 4,379,462 to Borkan et al. shows a catheter electrode assembly for spinal cord stimulation which, unlike the present invention, does not include a channel for drug delivery. Frequencies ranging from 10 to 1400 Hz are applied in the stimulation.

International application WO 92/07605 shows an epidural catheter intended to be implanted either temporarily or permanently. In a permanently implantable embodiment, the catheter includes an implantable pulse generator and, at a separate branch of the catheter, an implantable drug reservoir.

U.S. Pat. No. 5,423,877 to Mackey shows a catheter for use in acute pain management intended for electrical stimulation of the epidural space of the spinal cord. The catheter comprises a conduit for delivery of drugs. The catheter produces a longitudinally elongated electrical field, as leads of the catheter will electrically stimulate a longitudinal distance of from 10 to 15 cm. However, this is not suitable for selective stimulation of nerves.

U.S. Pat. No. 5,374,285 to Vaiani et al. discloses a spinal electrode catheter which can be connected to a stimulator.

U.S. Pat. No. 5,081,990 to Deletis shows a catheter for spinal epidural injection of drugs and measurement of evoked potentials. Measuring electrodes located on the tip of the catheter are connected to a voltage detector. The electrodes are, however, not adapted for electrical stimulation.

German patent application DE 36 02 219 A1 shows a flexible epidural neuroelectrode comprising a channel with lateral apertures. The electrode or catheter allows to administer pharmacological solutions epidurally and to measure the evoked spinal potentials at the same time (spinal cord monitoring). The electrode is, however, not adapted for electrical stimulation.

European patent application 1 145 731 A2 shows a multi-lumen, multi-functional catheter system. The catheter system is intended for use for a therapy of the parenchymal tissues of the brain. Amongst the generally mentioned uses is sampling of fluids within the extracellular and interstitial spaces of the brain, spinal cord, or other body tissues, concurrently with drug delivery or electrical recording/stimulating. Information gathered by a sensing element or measuring device is received by a host computer to evaluate a treatment procedure or patient conditions around the locality of treatment. A treatment procedure would be evaluated either by an operator or by artificial intelligence. Possible sensing systems include thermometric sensing systems. However, unlike the present invention, the application EP 1 145 731 A2 does not provide for a flexible epidural catheter having electrical contacts for stimulation.

Unlike the present invention, none of the documents described above does provide for the usage of high frequency (radio frequency) energy for electrical nerve stimulation. Also none of these documents describes a flexible catheter comprising a temperature sensor disposed in the distal region of the catheter. Actually, only the European application EP 1 145 731 A2 mentions thermometry at all.

SUMMARY OF THE INVENTION

It is an object of the present invention to provide a flexible catheter for treatment of a nervous system, which is suitable for a larger range of application than conventional catheters, electrodes or special needles, and a method for treatment of a nervous system using said catheter.

A further object of the invention is to provide a catheter which is adapted for stimulation with pulsed high frequency.

A further object of the invention is to provide a catheter and a method for applying pulsed radio frequency energy to a region in the spinal canal.

A further object of the invention is to provide a flexible lead for treatment of a nervous system, which is suitable for a larger range of application than conventional catheters, electrodes or special needles, and a method for treatment of a nervous system using said lead.

A further object of the invention is to provide a method of treatment of a nervous system for treating a large range of medical conditions.

A further object of the invention is to provide a method of treatment of a nervous system for treating a large range of organs of the body.

The objects of the present invention are achieved by providing a flexible catheter, particularly a flexible epidural catheter, according to the present invention, which comprises at least two electrical contacts in a distal region of the catheter; leads of the electrical contacts are located inside the catheter; two of the leads have a connection for a high frequency pulse generator for nerve stimulation.

In one embodiment, the stimulation catheter for insertion in a body is part of a stimulation system, the system further comprising an external contact; said external contact being adapted to be exposed to an external part of said body. With this system, for example, pulsed high frequency can be applied between said contact in a distal region of the catheter and said external contact. Moreover, nerve conduction can be measured beginning at the nerve root.

When said flexible catheter forms a part of a flexible probe having at least a second lead and at least a second electrical contact, said radio frequency energy can be applied between said first and second contacts. Pulsed high frequency can be applied between said two contacts using a bipolar signal generator, for example.

A catheter having at least one electrical contact at a distal region is suited for usage with a unipolar pulse generator like, for example, one of the device N50 of the company Stryker Howmedica, the device RFG-3C+ of the company Radionics, and the device Neurotherm of the company RDG Medical.

Preferably, the catheter of the invention is adapted to be inserted into one of an epidural space, a spinal space, a paravertebral space, an intracerebral region, and regions of ganglia of the head or neck.

Preferably, the catheter is an epidural catheter. When such a catheter is inserted into the region of the spinal canal, it is possible to apply a pulsed high frequency current via two electrical contacts to the spinal cord or the spinal nerves instead of or additionally to the injection of pain-killing drugs, according to requirements. Thus, by stimulating the nerves inside the spinal canal, in many cases a treatment or stimulation of nerve tissue with special needles outside the spinal column or in dangerous regions can be avoided, and also those nerves can be treated with high frequency pulses which otherwise would not have been accessible for this treatment. Thus, the catheter according to the invention opens up a distinctly enlarged range of application as compared to a conventional catheter or conventional needles.

The catheter enables the stimulation of spinal dorsal nerve roots proximal to the spinal nerve ganglia with radio frequency and allows to apply pulsed radio frequency (PRF) in the spinal canal and other targets. New treatments are thus possible. With the catheter and the PRF it is possible to reach vulnerable structures and to treat them with PRF without fear of damaging them.

The invention includes providing a method for applying pulsed radio frequency energy to a region of the spinal canal, this method comprising the steps of:
  inserting a flexible epidural catheter into said region, said catheter having at least two electrical contacts in a distal region of the catheter;
  operating a pulsed radio frequency generator; the pulsed radio frequency generator being coupled to the electrical contacts; thereby applying pulsed radio frequency energy via said electrical contacts to at least one of the spinal cord or spinal nerves;
  whereby in said region at least one of the spinal cord or spinal nerves is treated.

In one embodiment, the method further comprises the step of probing a position of the catheter by applying a test stimulation signal via said electrical contacts and thereby probing a sensual response to the test stimulation signal; thereby gaining information about the position of the catheter relative to the at least one of spinal nerves and a part of a spinal cord which is to be treated. Preferably, the test stimulation signal is applied between two electrical contacts in the distal region of the catheter, even if the pulsed high frequency energy is applied between one of these contacts and an external contact.

A method for applying pulsed radio frequency energy to at least one of a nerve, a nerve root, a nerve ganglion, and a part of a spinal cord in a space of a spinal canal can be carried out following the steps of:
  inserting a flexible catheter percutaneously into said space, the catheter having at least one electrical contact at its distal region;
  then pushing the catheter forward, thereby positioning said at least one contact in the spinal canal;
  adjusting the catheter such that said at least one electrical contact is in a region of the at least one of a nerve, a nerve root, a nerve ganglion, and a part of the spinal cord; and
  operating a pulsed radio frequency generator, thereby applying pulsed radio frequency energy via the at least one electrical contact to the region of the at least one of a nerve, a nerve root, a nerve ganglion, and a part of a spinal cord. Thereby, the at least one of a nerve, a nerve root, a nerve ganglion, and a part of a spinal cord is treated.

In one embodiment of this method, the method further comprises a step of repeatedly adjusting the catheter to different positions. Thereby, several of nerve roots and parts of the spinal cord can be treated, for example, one after another, without having to insert the catheter twice.

The invention includes providing a flexible endoscopic probe. The endoscopic probe comprises at least one electrical contact in a distal region of the probe, a connection for a high frequency pulse generator for nerve stimulation; and at least one electrical conductor running inside the probe: the conductor connecting said at least one contact to said connection. The endoscopic probe allows to position the contact under endoscopic control and to apply pulsed high frequency endoscopically. Preferably, the endoscopic probe is compatible to standard light cables. The endoscopic probe can also be combined with the catheter to one combined catheter/endoscopic probe for stimulation with pulsed high frequency. In one embodiment, the endoscopic probe is at least a double lumen probe. One lumen contains an optical conductor, and another lumen contains a lead or the electrical conductor, thereby constituting a lead.

The same methods as described above can be applied using a lead without a lumen for transport of liquid instead of the catheter. By inserting a flexible lead into one of an epidural space, spinal space, paravertebral space, intercerebral region and ganglia of the head and neck, it is possible to treat at least one of a nerve, a nerve root, a nerve ganglion, a part of the spinal cord and a part of the brain, for example.

The lead can also pass through an endoscopic probe. This allows to position the lead under endoscopic control and to apply pulsed high frequency endoscopically.

In one embodiment of the method, the lead further comprises a temperature sensor at the distal region of the lead, leads of the temperature sensor being located inside the lead, and the method further comprises the step of:

monitoring a temperature using the temperature sensor at the distal region of the lead;

wherein in the step of operating the pulsed radio frequency generator, the pulsed radio frequency energy is applied depending in a predetermined way on the monitored temperature.

In another embodiment, the method comprises the steps of: displacing the lead to a second localized region; and then repeating the step of operating the pulsed radio frequency generator;

whereby in said second localized region at least one of a nerve, a nerve root, a nerve ganglion, a part of the spinal cord and a part of the brain is treated.

Indications and targets for application of pulsed radio frequency with the invented catheter, lead and method are: pain treatment, diagnostic and therapeutic stimulation, injection of medicaments. All locations in the spinal canal from the medulla oblongata to the hiatus sacralis can be treated. In particular, indications and targets are: treatment of sympathetic and parasympathetic nerves and fibers in vascular diseases, treatment of spasticity, treatment of spastic and motor disorders and pain in: the brain, midbrain, thalamus, hypothalamus, gasserian ganglion, cerebellum, medulla oblongata, spinal cord, nerve roots and nerves in the spinal canal, retrograde and direct stimulation of the dorsal root ganglia, dorsal root entry zone (DREZ), stimulation of the dorsal column. For some of these uses, little modifications of the catheter are needed, as will be apparent to those skilled in the art.

Generally the indication is presently estimated to be at least similar to all indications of the PRF and temperature denervations. In addition following treatments are possible: radicular diseases as the post herpetic neuropathy, mono- or polyneuropathies, complex regional pain syndrome (CRPS), neuralgia, ischaemic disease, pain, spasticity and motor disorders.

Generally, the pulse radio frequency energy may be applied to a localized region for treatment of a medical condition that is related to and influenced by at least one of a nerve, a nerve root, a nerve ganglion, a part of the spinal cord and a part of the brain, which is treated in said localized region. That is, the medical condition to be treated, for example a disease, may be affected, controlled, modified or caused by the central or peripheral nervous system. One example of such a medical condition is a neurogenic disorder.

Medical conditions that are related to a nerve, a part of a nerve or of the central of peripheral nervous system include indications and targets that have been mentioned above. For example, the medical condition may be pain, for example chronic pain, neuralgia, and the complex regional pain syndrome (CRPS).

Other medical conditions are those that are related to a nervous disorder or a neuro-muscular disorder, such as radicular diseases and mono- and polyneuropathies.

The medical condition may be also a movement disorder or a motor disorder, for example, spasticity and spastic and motor disorders.

Further medical conditions that are related to and influenced by a central or peripheral nervous system are vascular diseases and circulatory disorders, for example, ischemec disease.

Although one of the main benefits of the application of pulsed radio frequency is treating neuropathic pain, it has been found that the lead and the catheter of the invention are also advantageous in treating patients with other diseases having a connection to the nerve system. Amongst these diseases are cases where pain is not the main symptom.

The central or peripheral nervous system can cause or modify many conditions. It has been found that treating the spinal cord or the dorsal roots or other nerves with pulsed radio frequency can interfere with the diseases which are maintained by these nerves.

In one embodiment of the method of the invention, the pulsed radio frequency energy is applied to the localized region for treatment of a medical condition that is related to and influenced by the at least one of a nerve, a nerve root, a nerve ganglion, a part of the spinal cord and a part of the brain, wherein the medical condition is connected with an organ of the body that is associated with the at least one of a nerve, a nerve root, a nerve ganglion, a part of the spinal cord and a part of the brain.

For example, the medical condition is at least one of:
disorders of bladder function,
disorders of micturition,
disorders of bladder sensation,
disorders of detrusor functions,
neuropathic bladder,
urinary incontinence,
detrusor-sphincter dyssynergia, and other sphincter dysfunctions,
disturbances of micturition due to disorders of the central nervous system,
disorders due to spinal cord injury,
disorders due to spinal cord diseases,
idiopathic bladder disease, idiopathic sphincter disease,
disorders of erection and ejaculation,
interstitial cystitis and other visceral pain syndroms,
central and peripheral vascular diseases,
anal pruritus, and
fecal incontinence.

Preferably, the pulsed radio frequency energy is applied to the localized region for treatment of an organ of the body that is innervated by the at least one of a nerve, a nerve root, a nerve ganglion, a part of the spinal cord and a part of the brain.

In another embodiment of the method of the invention, the pulsed radio frequency energy is applied to the localized region for increasing the blood circulation in a part of the body, said part of the body being associated with the at least one of a nerve, a nerve root, a nerve ganglion, the part of the spinal cord and a part of the brain. Thereby, a dilatation of peripheral blood vessels or hyperemia may be effected.

Preferably, the catheter of the invention further comprises a distal aperture of at least one hose line being located between two of the contacts. Such an arrangement allows to treat the same area with drugs as well as with high frequency stimulation without having to alter the location of the catheter. Moreover, due to the proximity of the contacts to the distal aperture of the catheter, the advantage results that during insertion of the catheter, the location of the catheter can be probed via a test stimulation with reduced voltage and frequency. Thus, stimulation can serve to localize the pain or the pain conducting nerves, and in this manner, a preferably well suited position for the catheter can be found. Another advantage is that the x-ray contrast of the contacts is sufficiently high to allow positioning of the catheter with x-ray monitoring without application of a contrast agent.

Preferably, the contacts of the catheter are disposed in a row along the longitudinal direction of the catheter. Preferably, the catheter ends at its distal end with a contact the outer surface of which has the shape of a cap. At least one of the contacts preferably has an outer surface having the shape of an annular strip encircling the catheter.

Preferably, the catheter is also connectable to pulse generators being applicable for permanent stimulation of nerves.

Several possible and advantageous configurations of the catheter are conceivable. For example, the leads of the contacts can be disposed within a hollow space of the catheter which is separated from the inner space of each hose line. The leads of the contacts can also run within the wall of the catheter. The catheter can also comprise a hose line in the form of a tube disposed within the catheter and, for example, filling a hollow space of the catheter.

Preferably, the outer diameter of the catheter is less or equal 1.67 mm, more preferably 1.33 mm, and the catheter preferably has a length of at least about 60 cm. Preferably, the contacts are disposed one after another at a distance of a few millimeters along the longitudinal direction of the catheter. Preferably, said distance is 4 mm.

In an embodiment of the invention, the catheter further comprises a temperature sensor in the distal region of the catheter; leads of the temperature sensor are located inside the catheter.

Thus, with the catheter further comprising a temperature sensor at the distal region of the catheter, leads of the temperature sensor being located inside the catheter, a method as described above can be carried out, the method further comprising the step of monitoring a temperature using the temperature sensor at the distal region of the catheter, wherein in the step of operating the pulsed radio frequency generator, the pulsed radio frequency energy is applied depending in a predetermined way on the monitored temperature.

For example, at least one parameter of the pulse generation is automatically changed when a specific temperature has been reached.

When the epidural catheter comprising the temperature sensor is inserted into the area of the spinal canal, and a pulsed high frequency current is applied to the spinal cord or the spinal nerves via two contacts, an increase of temperature caused by the stimulation or effected by the applied electrical energy can be monitored by means of the temperature sensor. For example, a temperature monitoring circuit or device can be provided which automatically switches off or temporarily suppresses the stimulation when an upper temperature limit of 42° C. is reached so as to avoid thermal damaging of the tissue.

By monitoring the tissue's temperature using a temperature sensor, nerves or the spinal cord can be treated with pulses or pulsed high frequency the parameters of which can be varied within larger boundaries without having to worry about thermally damaging the tissue. Thus it is possible to optimally adapt the intensity of the stimulation to the needs of the patient, especially when using pulsed high frequency which is high in energy. Such frequency can also be used with frequently repeated stimulation or permanent stimulation over a longer time, because an accumulated rise of temperature can reliably be monitored. Even if the electrical parameters of the tissue change due to adsorption of tissue or modification of the local tissue structure, and more energy is introduced due to a higher conductive loss, damaging can be avoided because of the temperature monitoring. Thus, the invented catheter opens up a still larger range of application compared to a conventional stimulation catheter.

Preferably, the temperature sensor is a thermocouple, for instance of the type nickel-chromium/nickel. The advantage of a thermocouple is that its thermal voltage is independent of the geometry of the point of contact of the two leads. Moreover, the thermocouple can be manufactured with very thin wires having an accordingly low thermal inertia, resulting in immediate detection of an increase of temperature. Since a thermocouple is an active sensor, conducting resistance is unproblematic. The leads of the temperature sensor can be the wires of the thermocouple.

Preferably, the temperature sensor is thermally connected to one of the electrical contacts. In this way, the temperature can be measured directly at the heated spot, and a good thermal contact is achieved.

One of the connecting leads of the temperature sensor can also serve as a lead of one of the electrical contacts. Thereby, one lead is saved.

The leads of the contacts and/or the connecting leads of the temperature sensor can be disposed within a hollow space of the catheter which is separated from the inner space of each hose line. The leads of the contacts and/or the connecting leads of the temperature sensor can also run within the wall of the catheter.

In another embodiment the catheter comprises a transducer; the electrical contacts are connected via the leads to the transducer, and the transducer is adapted to be subcutaneously implanted and is adapted to transmit high frequency pulses for nerve stimulation onto the leads; the catheter further comprises a port in a proximal area of the catheter; the port is adapted to be subcutaneously implanted. Preferably, the catheter is an epidural catheter.

After insertion of the catheter, the catheter can be completely implanted, including the transducer and the port, beneath the skin near to the point of entrance into the body. When later using the catheter for stimulation of the spinal cord or of nerves, for example, the risk of infection is reduced due to the closed skin and the risk of complications is reduced. Moreover, the catheter being concealed below the skin is easier to handle for the patient.

When such a catheter is inserted as an epidural catheter into the area of the spinal canal, for example, in addition to stimulation of the spinal cord or the spinal nerves by means of a pulsed high frequency current, injection of a pain-killing drug via the port can take place, according to requirements. The implanted port can, for example, be configured in form of a septum, which can be reached from external and pierced with a injection needle.

Thus, this embodiment of the catheter has further distinct advantages of usage over a conventional catheter and thereby opens up an even further range of application.

Optionally, between the port and the catheter, a drug pump can be provided being likewise implantable. Thereby, an evenly distributed dispensing of drugs is achievable over a longer time period.

Optionally, the transducer comprises a device for storing energy. This device can effect the energy supply of a drug pump, for example.

The high frequency pulses can be transmitted inductively from an external device to the transducer, for example. Alternatively, energy can be supplied inductively to the transducer, and the transducer itself generates the pulses for nerve stimulation.

The transducer can also comprise a pulse generator for stimulation or permanent stimulation of nerves.

Preferably, the transducer comprises a coil. In particular, the coil can be a coil for sending and receiving. Thus the coil being utilized for sending, the catheter is adapted to send signals to a device outside the body.

Preferably, the catheter further comprises a temperature sensor in the distal region of the catheter, and leads of the temperature sensor are located inside the catheter. The feature of the temperature sensor and advantageous applications have been described above in detail. Preferably, the transducer is adapted to receive a signal effected by the temperature sensor.

For monitoring the temperature the transducer can send signals to an external device, and a monitoring circuit can be provided externally or disposed within the transducer, said monitoring circuit automatically switching off or temporarily suppressing the stimulation when an upper temperature limit of 42° C., for example, has been reached, so that thermal damaging of the tissue can be avoided.

Preferably, the transducer is adapted to receive an electrical signal from the electrical contacts. Thereby, a measurement of an excitation potential of a nerve can take place, for example.

In a preferred embodiment the catheter further comprises an injection chamber for the catheter being located at the port. Thereby, the injection of drugs via the port is facilitated and the injection chamber can also serve as a reservoir chamber for an implantable drug pump.

In a preferred embodiment, the transducer and the port are disposed in a flat casing being subcutaneously implantable. The combination of the port and the transducer in one casing facilitates locating them in case a drug is to be injected into the catheter, for example. Furthermore, the casing can accommodate the coil of the transducer, for example, and can serve as a supporting surface for the injection chamber or for the port, thus facilitating the handling when introducing an injection needle into the port.

All embodiments of the catheter or lead mentioned above can be implanted to remain in the body for a period of, for example, up to several days or weeks. In this way, high frequency pulses can be applied at several times.

Further scope of the applicability of the present invention will become apparent from the detailed description of preferred embodiments of the invention given hereinafter. However, it is to be understood that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only and thus are not limiting of the present invention and wherein

FIG. 8 is a schematic view of an embodiment of an epidural catheter having a transducer with a coil within a flat casing being subcutaneously implantable, as well as an external device having an antenna;

FIG. 9 is another view of the casing and the transducer with the coil;

FIG. 10 is a schematic view of a stimulation lead passing through an endoscopic probe; the lead having one electrical contact and a thermocouple;

For reasons of clarity, the drawings are not drawn to scale.

DETAILED DESCRIPTION OF PREFERRED EMBODIMENTS

Figure 1:
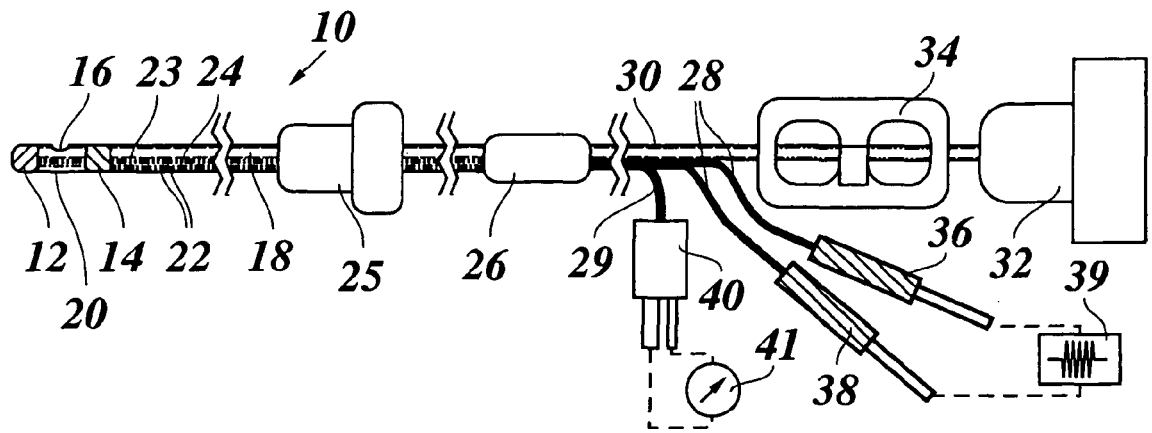
FIG. 1 is a schematic view of an epidural catheter having two contacts, a thermocouple, and a hose line.

FIG. 1 shows an epidural catheter 10 comprising in its distal region a distal contact 12 and a proximal contact 14 between which a lateral aperture 16 of a hose line 18 is disposed. Contacts 12 and 14 are drawn with hatching. The distal contact 12 forms a cap encasing the end of the catheter 10. The proximal contact 14 forms an annular strip encircling the catheter 10. The edges of the contacts 12 and 14 are flush with a mantle 20 of the catheter 10 made of silicone rubber.

The outer diameter of the mantle 20 is 1.33 mm, corresponding to a specification of 4 French. In longitudinal direction of the catheter 10 the contacts 12 and 14 extend to a length approximately corresponding to the outer diameter of the mantle 20. The contacts 12 and 14 are offset to each other by approximately 4 mm in longitudinal direction of the catheter 10. The overall length of the shown epidural catheter 10 is 60 cm, however, other lengths are also conceivable.

Within the catheter 10, a thermocouple 21 (FIG. 2) is thermally connected to the distal contact 12. Electrical leads 22 for the electrical contacts 12, 14 as well as connecting wires 23 and 24 of the thermocouple 21 run within the mantle 20 parallel to hose line 18 and are, like hose line 18, indicated with dashed lines in FIG. 1. Thermocouple 21 is of the type nickel-chromium/nickel, wire 23 being of nickel-chromium and wire 24 being of nickel. The internal configuration of catheter 10 will be further explained below with FIGS. 2 and 3.

Catheter 10 comprises a fixation device 25 which can serve to fasten the catheter to a point where the catheter enters a body, the element 25 being configured like in a conventional implantable catheter. Furthermore, in a known manner an aseptic guide wire (not shown) is disposed within the hose line that serves to push the catheter 10 to the desired position in the spinal canal and is then retreated. The guide wire is slightly bendable in the region of its leading end.

At a connecting member 26, the electrical leads 22 are led out of the mantle 20 of catheter 10 in form of electrically isolated wires 28, and wires 23 and 24 are led out of the mantle 20 into an isolated cord 29. The hose line 18 continues within a mantle 30, which is a continuation of mantle 20, to a connector 32. Said connector serves for connecting a syringe or a drug pump and is configured in a conventional manner. Between the connector 32 and connecting member 26 is disposed a clip 34 that allows to clamp hose line 18 and re-open it by releasing clip 34. The clip 34 is configured in a conventional manner, as well, and can also be disposed at the connection 32.

Wires 28 are provided with electrical connectors 36 and 38. Connector 36 is connected to the distal contact 12, and a connector 38 is connected to the proximal contact 14 of the catheter. Connectors 36 and 38 are merely schematically shown in the drawing, and can be encoded in terms of color and/or in terms of the shape of contacts of the connectors. Said connectors are adapted to be directly or via an adapter (not shown) connected to a pulse generator 39 generating a pulsed high frequency current. The pulse generator 39 can, for example, be the device N50 of the company Stryker Howmedica, the device RFG-3C+ of the company Radionics, or the device Neurotherm of the company RDG Medical.

The connectors 36, 38, wires 28, leads 22, and the contacts 12 and 14 are adapted both for application of pulses for a test stimulation of nerves or of a spinal cord having, for example, a voltage in the range of 0 to 12 V, a frequency in the range of 50 to 150 Hz, and a pulse width in the range of 150 to 400 microseconds, as well as for applying pulsed high frequency, for example, within a voltage ranging from 20 to 30 V and a pulsed frequency of 500 kHz and a pulse width of 20 ms. The numerical values given are only examples to illustrate the range of application of the catheter.

A bipolar connector 40 of cord 29, being secured against connecting with the wrong polarity, is connected to the wires 23 and 24 of the thermocouple 21. Connector 40 is adapted for connecting to a measuring device 41, which measures the temperature in the region of the distal contact 12 of the catheter using the thermocouple 21.

The measuring device 41 can be integrated into the pulse generator 39 in form of an appropriate circuit, for example, or can be connected to the pulse generator, so as to automatically effect a switching off or a change of parameters of pulse generation when a specific temperature is reached; said specific temperature being adjustable. For example, an adaptive or stepwise control of pulse generation can be provided that reduces the power and/or frequency of the pulses when an intended upper temperature limit is approached. Alternatively or, if the temperature is too high, additionally the pulse generation can be temporarily stopped until a sufficiently low temperature is reached again.

Figure 2:
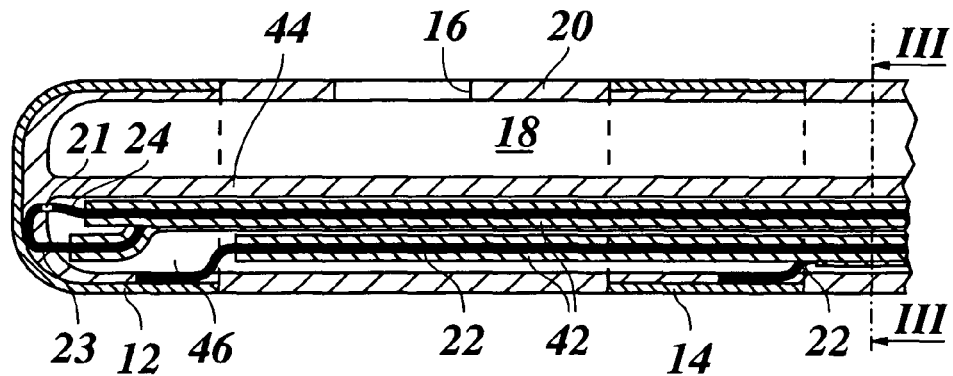
FIG. 2 is a schematic longitudinal sectional view of a tip of a first embodiment of an epidural catheter.

FIG. 2 shows the tip of the catheter 10 of FIG. 1 as a longitudinal sectional view, though the catheter 10 as well as the leads 22 and wires 23, 24 disposed in front of and behind the plane of the drawing are shown in a sectional view.

The electrical leads 22 and wires 23, 24 each comprise an isolation 42. Leads 22 are internally soldered to the distal contact 12 and the proximal contact 14 respectively. The thermocouple 21 is formed by a contact point of the nickel-chromium wire 23 and the nickel wire 24 and is connected to the contact 12 via the wire 23 in immediate proximity. Thus, a good heat conduction between the contact 12 and the thermocouple 21 is accomplished.

The mantle 20 of the catheter 10 comprises an internal partition wall 44 dividing the inside of the catheter 10 into a first hollow space forming the hose line 18 and a second hollow space 46. The leads 22 and wires 23, 24 run within this second hollow space 46. The electrical contacts 12 and 14 are separated from the hose line 18 by the mantle 20. The lateral aperture 16 of the mantle 20 opens the hose line 18 to the outside.

Figure 3:
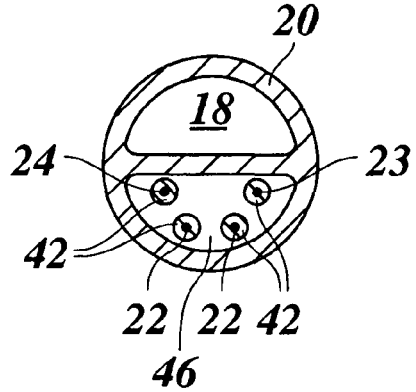
FIG. 3 is a transverse sectional view of the catheter of FIG. 2.

FIG. 3 shows a cross-sectional view of the catheter 10 along the line III-III of FIG. 2. The arrangement of leads 22 and wires 23, 24 within the second hollow space 46 of the mantle 20 is shown.

Figure 4:
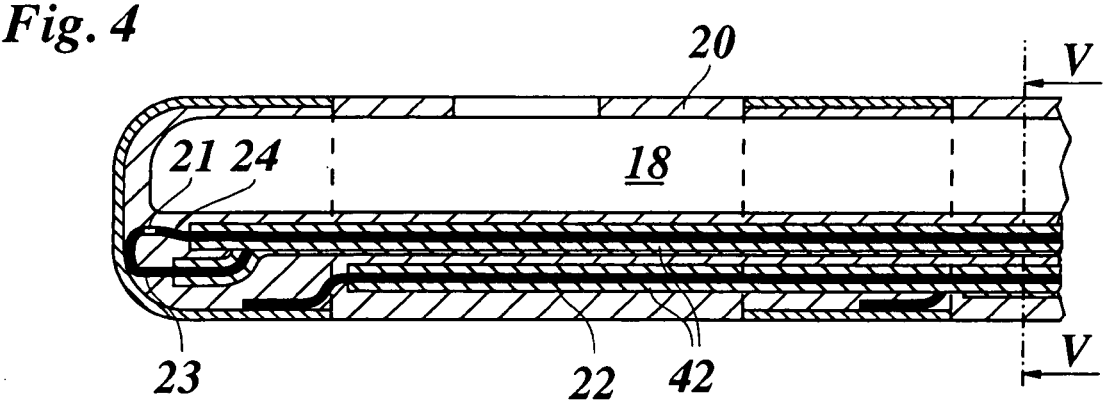
FIGS. 4 and 5 show a second embodiment of a catheter in views corresponding to FIGS. 2 and 3.
Figure 5:
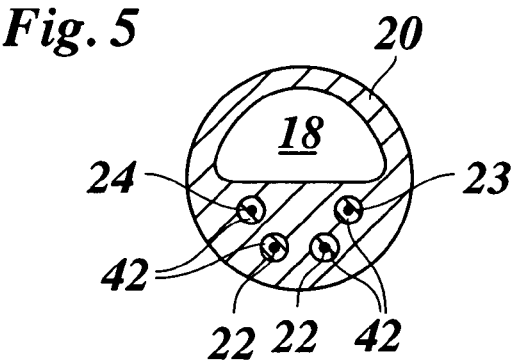

FIGS. 4 and 5 show a second embodiment, wherein the mantle 20 has no internal partition wall 44 forming a second hollow space 46. Instead the electrical leads 22 and the wires 23, 24 with their respective isolations 42 run within a thickened area of the wall of the mantle 20 of the catheter 10. The hose line 18 is formed inside the mantle 20 in a way similar to the first embodiment.

Figure 6:
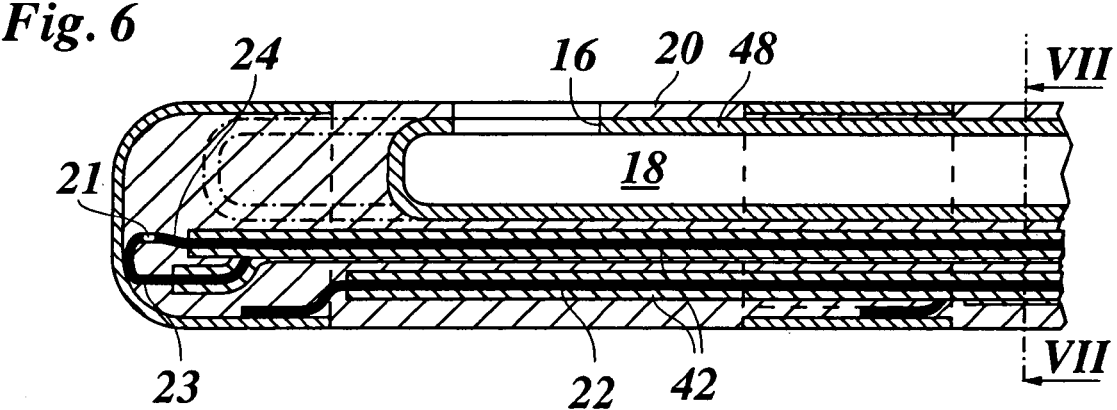
FIGS. 6 and 7 show a third embodiment of a catheter in views corresponding to FIGS. 2 and 3.
Figure 7:
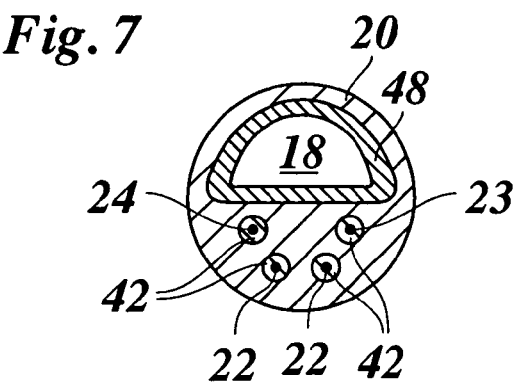

FIGS. 6 and 7 show a third embodiment which differs from the second embodiment in that inside the mantle 20, there is an additional internal tubular layer 48 forming the hose line 18. The mantle 20 encloses the tube formed by the internal layer 48 as well as the isolations 42 of the electrical leads 22 and wires 23, 24. At least at the aperture 16, which penetrates the layer 48 and the mantle 20, the internal layer 48 is tightly connected to the mantle 20. However, the internal layer 48 can also be a part of a mantle of the catheter constituted of two or more layers.

The tube formed by the inner layer 48 ends on the other side of the aperture 16. It can, however, also extend into the cap formed by the distal contact 12 as indicated by chain dotted lines. The internal layer 48 is isolated by the mantle 20 from the contacts 12 and 14.

The shown embodiments are meant to demonstrate a possible arrangement and contacting of the electrical leads 22 and of the thermocouple 21 and its wires 23, 24 and to present possible constructions of the hose line 18. It is to be understood that the catheter of the invention can also have a configuration that differs from these embodiments, for example a combination of the inner layer 48 of FIG. 7 with the two hollow spaces of the mantle 20 of FIG. 3, or a different location of the thermocouple 21.

Alternatively, the electrical contact 12 can also be configured having the shape of an annular strip. It goes without saying that more than the two shown contacts can be provided.

FIGS. 8 and 9 show another embodiment of the catheter 10 the distal part of which is constituted similar to the catheter of the third embodiment shown in FIGS. 6 and 7.

As the proximal end of the catheter 10, the catheter is seamlessly connected to a flat casing 52. The upper region of the casing 52 contains an injection chamber 54 which is connected to the hose line 18. The upper wall of the injection chamber 24 comprises a bulge forming a port 56 in form of an injection septum. Via the port 26, the injection chamber of the implanted catheter is accessible from external by way of an injection needle, for example. The injection septum is made in a known manner such that its wall is sufficiently dense and elastic so as to provide a reliable sealing after an injection needle previously inserted through the septum is retracted.

In the lower region of the casing 52 a coil 58 is arranged spirally, as can be seen more clearly in FIG. 9. The coil 58 is a sending and receiving coil and is connected to a transducer 60. The transducer 60 has several functions which will be explained hereinafter.

At the casing, an aperture for introducing the guide wire is closed before implanting the casing.

The electrical leads 22 and the wires 23, 24 are connected to the transducer 60. The transducer is adapted to measure currents and/or voltages. For example, the transducer 60 can measure a thermovoltage on the wires 23 and 24 of the thermocouple, thereby monitoring the temperature at the distal end of the catheter 10. The transducer 60 can also measure potentials between the electrical contacts 12 and 14, for example. Such potentials can provide information about the excitation condition of nerve roots or the spinal cord, for example.

The transducer 60 is addressed by an external device 70 comprising an antenna 72 cooperating with the sending and receiving coil 58 of the transducer 60. The pulse generator 39 and indication devices 76 are connectable to the external device 70.

The pulse generator 39 produces a pulsed high frequency current. The high frequency pulses are inductively transmitted by the antenna 72 to the coil 58 and are relayed by the transducer 60 to the leads 22 of the electrical contacts 12 and 14. The contacts 12 and 14, the leads 22, and the transducer 60 and the coil 58 are adapted both for application of pulses for a test stimulation of nerves or of a spinal cord having, for example, a voltage in the range of 0 to 12 V, a frequency in the range of 50 to 150 Hz, and a pulse width in the range of 150 to 400 microseconds, as well as for applying pulsed high frequency, for example, within a voltage ranging from 20 to 30 V and a pulsed frequency of 500 kHz and a pulse width of 20 ms. The numerical values given are only examples to illustrate the range of application of the catheter.

During pauses in-between the pulses and at times where no stimulation takes place, the transducer 60 can send signals via the coil 58 to the external device 70, which receives the signals by means of its antenna 72. Information can be transmitted concerning the temperature measured by the temperature sensor as well as information concerning electrical signals the transducer 60 receives from the electrical contacts 12 and 14. Furthermore, further signals can be transmitted from the transducer 60 to the external device 70 or in the opposite direction for control purposes, for example. The indication devices 76 can display measured voltages, currents or temperatures.

In case the transducer 60 detects that an allowable maximum temperature of the temperature sensor 21 is exceeded, the transducer 60 can effect an automatic switching off or changing of parameters of pulse generation of the pulse generator 39 by means of control signals, for example. Thus, an adaptive or stepwise control of pulse generation can be provided that reduces the power and/or frequency of the pulses when an intended upper temperature limit is approached. Alternatively or, if the temperature is too high, additionally the pulse generation can be temporarily stopped until a sufficiently low temperature is reached again.

FIG. 9 shows the casing 52 of the catheter 10 of FIG. 8 as viewed from the bottom of FIG. 8. The spiral configuration of the coil 58 is visible.

FIG. 10 shows an endoscopic probe 80 with a light conductor 82 that contains optical fibers for light delivery and visualization, as is known in the art. However, the endoscopic probe 80 also comprises a stimulation lead 84 having a distal electrical contact 12 in the distal region of the probe 80. The light conductor 82 ends at the distal end of the probe 80.

The endoscopic probe 80 and the stimulation lead 84 are configured similar to the catheter 10 of FIG. 1, the major difference being that the hose line 18 is replaced by the light conductor 82. Therefore, similar parts are numbered with the same numbers as in FIG. 1, and the respective parts of the description of the catheter of FIG. 1 are included herein by reference. Another difference to the catheter 10 of FIG. 1 is that the stimulation lead 84 has only one contact 12 in its distal region. This contact 12 is connected to the connector 36. A second, external contact 86 is connected via a wire 88 to the connector 38.

Contact 12 forms an annular strip encircling the probe 80. A thermocouple is thermally connected to the contact 12. At the connecting member 26, the light conductor 82 continues within a light cable 90 that is compatible to standard light cables for endoscopy and ends at a connector 92.

Figure 11:
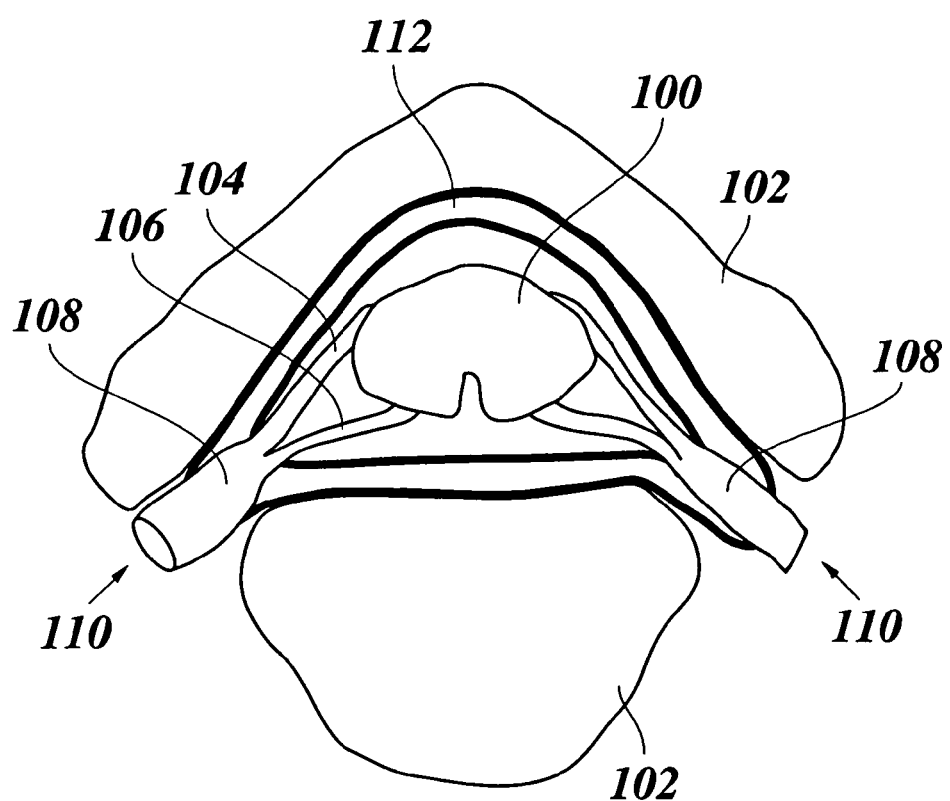
FIG. 11 is a cross-sectional anatomical view of a spinal cord in a spinal column.

FIG. 11 shows a sectional view of a spinal cord 100 and a spinal column at a level of a vertebra 102. Dorsal roots 104 and ventral roots 106 as well as spinal ganglia 108 of spinal nerves 110 are indicated. Within the spinal canal, an epidural space 112 is shown into which the catheter 10 is to be inserted.

Figure 12:
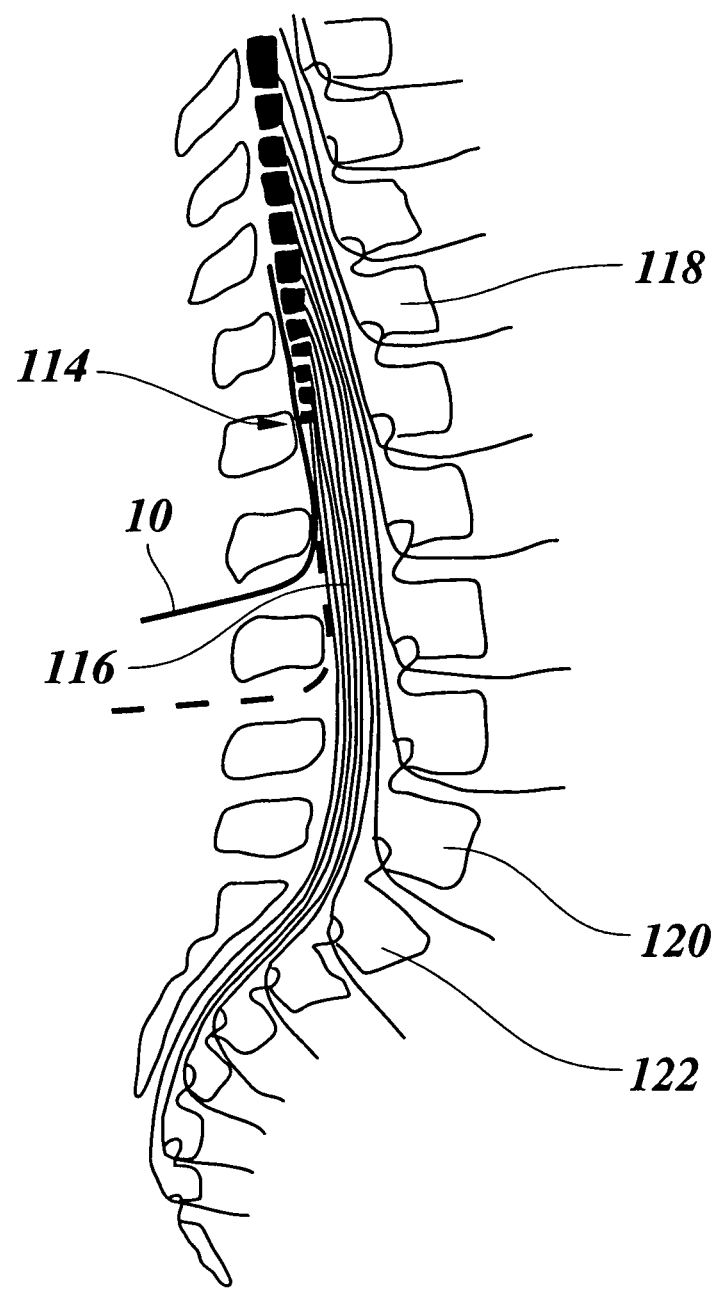
FIG. 12 is a sectional view of a spine taken along the length of the spine.

FIG. 12 schematically shows insertion of the partially shown catheter 10 into the spine. For example, the catheter 10 can be placed at the medullary conus 114 and cauda equina 116. The 12th thoracic vertebra 118, the 5th lumbar vertebra 120 and the 1st sacral vertebra 122 are indicated.

The catheter 10 can be inserted in a similar manner as conventional spinal cord stimulation (SCS) electrodes. A guide wire (mandrel) is used to steer the catheter in place and can be bent. The procedure is as easy as the placement of an SCS.

The inventor found out that it is plausible to place the catheter at the conus 114 and cauda equina 116. Here the nerve roots converge and can be treated by the passing catheter 10 one by one. Thus, the catheter is, for example, inserted at the contralateral or ipsilateral side into the mid-line of epidural space 112 or laterally and pushed obliquely upwards, passing the dorsal roots 104 of the spinal nerves 110. The catheter 10 is usually inserted under local or general anesthesia percutaneously through a Tuhoy needle by the loss of resistance technique into the epidural space 112. The catheter 10 is then pushed forward in an oblique way to lie at the dorso-lateral wall of the spinal canal.

The point of insertion of course depends on the nerves intended to treat. If, for example, it is intended to treat the lumbar nerves the catheter is introduced at the L2/3 space, as indicated in FIG. 12, pushing it up to the Th. 12 level, thus enabling to stimulate the nerves Th12 up to L 5. Or if it is intended to stimulate the sacral nerves the catheter has to be inserted at a deeper level L3/4, as indicated with a dashed line, pushing it up to the level L1. Then it is possible to treat the entire lumbar roots in addition to all sacral roots.

To be sure which nerves are affected they can be identified by stimulation with a frequency of 80 Hz, for example. The response of the patient is an accurate indication for the distances of the tip to the desired nerve.

After inserting and pushing upwards the catheter 10, at first the most cranial nerve root is stimulated and there, the PRF application is performed. Then, while stimulating, the catheter 10 is slowly retrieved. The sensations diminish and then when reaching the next nerve root rise again. There, the next PRF application is started. This procedure is repeated until all nerve roots positioned in the course of the catheter have been treated. The temperature sensor at the tip allows to be continuously informed about the temperatures at the tip.

The catheter 10 can be left in place up to 30 days. The procedures can be repeated at the same or any other level. It is also possible to add the catheter to an implantable device to repeat the PRF application at any time, as described herein before.

The catheter 10 is cannulated and allows to inject fluids, like steroids and other substances used in adhesiolysis, if desired. Medicaments can be injected as in any other catheter. Thus, it is possible to stimulate the dorsal nerve roots and ganglia proximal to the spinal ganglia and to apply PRF.

Especially when dealing with several segments and in difficult anatomical structures this flexible catheter is easier and safer to use. There are at least one ore more contacts at the tip of the catheter. The distal contact applies PRF and stimulation with all possible frequencies. This enables a very accurate positioning of the tip. Adapters can be provided for to connect the catheter to any radio frequency generator.

If intended for research, nerve conduction can be measured.

The catheter allows direct application of pulsed radio frequency to neural structures in the skull, the epidural space and in the spinal canal. This was until today impossible. It largely extends the use of radio frequency which was limited by using thermo-lesion needles outside of the epidural space, the spinal cord or canal. It is safer than heat and can be applied directly to the spinal cord. A permanent temperature control at the top of the catheter makes the procedure safe.

Adhesiolysis and the injection of steroids are possible. Exact placement by stimulation is another benefit of the catheter. The new oblique application technique could be of great therapeutic value.

With the catheter or lead of the invention, pulsed radio frequency may be applied for treatment of a medical condition that is related to and influenced by the central or peripheral nervous system. The indications and targets for application of pulsed radio frequency which have been mentioned above are confirmed by the following example of the treatment of a patient that suffered from a neurogenic bladder.

The female patient, born 1934, had a disk herniation at the L4/5 position in 1979. She suffered from a severe urinary retention due to a neurogenic bladder. The residual urine capacity was about 1000 ml. The patient could only void 50 ml spontaneously. In spite of several medication her problem could not be solved. A complete urological examination came to the conclusion that there was no possible cure except a conventional operation.

Then, in May 2004, the catheter was introduced via the sacral hiatus, and the S 2 to S 4 roots were stimulated by pulsed radio frequency.

Since that date slowly the conditions got better. The spontaneous urine was once 720 ml (03.11.2004) and once 580 ml (04.11.2004).

In addition to a nearly normalization of the conditions the patient was able to feel her urge to void from the first day on after the stimulation, which was a feeling she had missed for many years. At least this was described as a great improvement by the patient.

Furthermore, by the application of pulsed radio frequency according to the invention, a dilatation of peripheral blood vessels or hyperemia may be effected. This has been confirmed by the treatment of patients with pulsed radio frequency applied through the catheter of the invention. The patients felt a hyperemia in their feet, and a dilatation of their peripheral blood vessels was recognized.

The given examples also confirm that an organ being associated with or innervated by a part of a central or peripheral nervous system may be treated according to the invention.

The invention being thus described, it will be obvious that the same may be varied in many ways. Furthermore, all the disclosed elements and features of each disclosed embodiment of the catheter, stimulation system, lead, endoscopic probe or method can be combined with, or substituted for, the disclosed elements and features of every other disclosed embodiment of the catheter or method, respectively, except where such elements or features are mutually exclusive. Such variations are not to be regarded as a departure from the spirit and scope of the invention, and all such modifications as would be obvious to one skilled in the art are intended to be included within the scope of the following claims.

What is claimed is:

1. A method for applying pulsed radio frequency energy to a region in the spinal canal, comprising the steps of:
    inserting a flexible epidural catheter into a spinal space, said catheter having at least one first electrical contact in a distal region of the catheter and a distal aperture of at least one hose line;
    injecting pain killing drugs to a localized region to be treated via the distal aperture of the at least one hose line;
    operating a pulsed radio frequency generator, the pulsed radio frequency generator being coupled to said first electrical contact; thereby applying pulsed radio frequency energy via said first electrical contact to the localized region to be treated;
    detecting a temperature in the spinal space by a temperature sensor at the distal region of the catheter; and
    automatically changing at least one parameter of the pulsed radio frequency energy supplied to the localized region when a specific temperature is detected,
    automatically switching off or temporarily suppressing of the pulsed radio frequency energy to the localized region when an upper temperature limit of 42° C. is reached to thereby avoid thermal damage of tissue,
    whereby in said localized region at least one of a nerve, a nerve root, a nerve ganglion and a part of the spinal cord is treated.

2. A method as claimed in claim 1, wherein the pulsed radio frequency energy is applied to said localized region for treatment of a medical condition.

3. A method as claimed in claim 1, further comprising the step of probing a position of the catheter by applying a test stimulation via said electrical contact to detect a sensual response to the test stimulation signal.

4. A method as claimed in claim 3, wherein the test stimulation signal has a voltage in the range of 0 to 12 V, a frequency in the range of 50 to 150 Hz, and a pulse width in the range of 150 to 400 microseconds.

5. A method as claimed in claim 1, further comprising the step of repeatedly adjusting the catheter to different positions.

6. A method as claimed in claim 1, wherein the step of detecting the temperature comprises using a temperature sensor that is thermally connected to the first electrical contact.

7. A method as claimed in claim 1, wherein the step of inserting the flexible epidural catheter into the spinal canal comprises disposing an aseptic guide wire within the hose line, pushing the catheter to the desired position in the spinal canal, and retreating the guide wire.

8. A method as claimed in claim 1, wherein the step of injecting pain killing drugs uses a syringe or a drug pump.

9. A method as claimed in claim 1, wherein the applied pulsed radio frequency energy has a voltage in the range of 20 to 30 V, a frequency of 500 kHz and a pulse width of 20 ms.

* * * * *